(12) United States Patent
Shiraki et al.

(10) Patent No.: US 11,272,167 B2
(45) Date of Patent: Mar. 8, 2022

(54) INFORMATION PROCESSING APPARATUS, INFORMATION PROCESSING METHOD, AND INFORMATION PROCESSING SYSTEM

(71) Applicant: SONY CORPORATION, Tokyo (JP)

(72) Inventors: Hisakazu Shiraki, Kanagawa (JP); Takeshi Miyai, Kanagawa (JP); Kentaro Fukazawa, Tokyo (JP); Tadashi Morishige, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/313,611

(22) PCT Filed: May 23, 2017

(86) PCT No.: PCT/JP2017/019116
§ 371 (c)(1),
(2) Date: Dec. 27, 2018

(87) PCT Pub. No.: WO2018/008269
PCT Pub. Date: Jan. 11, 2018

(65) Prior Publication Data
US 2019/0246093 A1 Aug. 8, 2019

(30) Foreign Application Priority Data
Jul. 8, 2016 (JP) .............................. JP2016-135808

(51) Int. Cl.
*H04N 13/296* (2018.01)
*G03B 35/08* (2021.01)
(Continued)

(52) U.S. Cl.
CPC ............. *H04N 13/296* (2018.05); *G02B 7/28* (2013.01); *G03B 35/08* (2013.01);
(Continued)

(58) Field of Classification Search
CPC ............... H04N 13/204; H04N 13/218; H04N 2213/002; H04N 13/00
See application file for complete search history.

(56) References Cited

U.S. PATENT DOCUMENTS 9,693,036 B2 * 6/2017 Shibazaki ............... G03B 35/08
2010/0086293 A1 * 4/2010 Iwane ....................... G03B 3/00
396/91
(Continued)

FOREIGN PATENT DOCUMENTS

| CN | 103874960 A | 6/2014 |
| CN | 104756493 A | 7/2015 |

(Continued)

OTHER PUBLICATIONS

International Search Report and Written Opinion of PCT Application No. PCT/JP2017/019116, dated Aug. 22, 2017, 14 pages of ISRWO.
(Continued)

*Primary Examiner* — Kyle M Lotfi
(74) *Attorney, Agent, or Firm* — Chip Law Group

(57) ABSTRACT

There is provided an information processing apparatus including a control unit that controls display on the basis of a detection value indicating a focus state of a lens acquired from a stereoscopic imaging unit, and a captured image signal for a left eye and a captured image signal for a right eye acquired from the imaging unit.

16 Claims, 11 Drawing Sheets

(51) Int. Cl.
*H04N 13/00* (2018.01)
*H04N 13/218* (2018.01)
*H04N 5/232* (2006.01)
*H04N 13/225* (2018.01)
*G02B 7/28* (2021.01)

(52) U.S. Cl.
CPC ......... *H04N 5/23212* (2013.01); *H04N 13/00* (2013.01); *H04N 13/218* (2018.05); *H04N 13/225* (2018.05)

(56) References Cited

U.S. PATENT DOCUMENTS

| | | | |
|---|---|---|---|
| 2011/0175910 A1* | 7/2011 | Yahagi | H04N 13/296 345/419 |
| 2014/0055579 A1* | 2/2014 | Tezuka | H04N 13/128 348/51 |
| 2014/0192162 A1 | 7/2014 | Aoki et al. | |
| 2015/0245011 A1 | 8/2015 | Shibazaki et al. | |
| 2018/0077340 A1* | 3/2018 | Iwasaki | H04N 5/235 |
| 2018/0225838 A1* | 8/2018 | Ohara | G06T 7/593 |

FOREIGN PATENT DOCUMENTS

| | | |
|---|---|---|
| JP | 2010-056836 A | 3/2010 |
| JP | 2011-091463 A | 5/2011 |
| JP | 2012-178688 A | 9/2012 |
| JP | 2013-003170 A | 1/2013 |
| JP | 2013-130674 A | 7/2013 |
| WO | 2013/038863 A1 | 3/2013 |
| WO | 2013-038863 A1 | 3/2013 |
| WO | 2014/064946 A1 | 5/2014 |

OTHER PUBLICATIONS

Office Action for JP Patent Application No. 2018-525966 dated Jul. 13, 2021, 07 pages of Office Action and 07 pages of English Translation.

* cited by examiner

INFORMATION PROCESSING APPARATUS, INFORMATION PROCESSING METHOD, AND INFORMATION PROCESSING SYSTEM

CROSS REFERENCE TO RELATED APPLICATIONS

This application is a U.S. National Phase of International Patent Application No. PCT/JP2017/019116 filed on May 23, 2017, which claims priority benefit of Japanese Patent Application No. JP 2016-135808 filed in the Japan Patent Office on Jul. 8, 2016. Each of the above-referenced applications is hereby incorporated herein by reference in its entirety.

TECHNICAL FIELD

The present disclosure relates to an information processing apparatus, an information processing method, a program, and an information processing system.

BACKGROUND ART

Imaging devices having an autofocus (hereafter, may also be referred to as AF) function of automatically focusing on the subject have been used. For example, Patent Literature 1 discloses a technique for realizing an autofocus function in a stereoscopic imaging device having two imaging optical systems.

CITATION LIST

Patent Literature

Patent Literature 1: JP 2013-130674A

DISCLOSURE OF INVENTION

Technical Problem

However, if autofocus works in an imaging device during observation of captured images by the user, unfocused images are presented to the user. For example, in the case where images captured by a stereoscopic imaging device are displayed on a stereoscopic display device, unfocused images are difficult for the user to stereoscopically observe and may make the user uncomfortable.

Here, there are proposed an information processing apparatus, an information processing method, a program, and an information processing system that are novel, improved, and capable of alleviating discomfort that the user experiences during operation of autofocus.

Solution to Problem

According to the present disclosure, there is provided an information processing apparatus including: a control unit configured to control display on the basis of a detection value indicating a focus state of a lens acquired from a stereoscopic imaging unit, and a captured image signal for a left eye and a captured image signal for a right eye acquired from the imaging unit.

In addition, according to the present disclosure, there is provided an information processing method including: controlling display on the basis of a detection value indicating a focus state of a lens acquired from a stereoscopic imaging unit, and a captured image signal for a left eye and a captured image signal for a right eye acquired from the imaging unit.

In addition, according to the present disclosure, there is provided a program for causing a computer to realize: a function of controlling display on the basis of a detection value indicating a focus state of a lens acquired from a stereoscopic imaging unit, and a captured image signal for a left eye and a captured image signal for a right eye acquired from the imaging unit.

In addition, according to the present disclosure, there is provided an information processing system including: a stereoscopic imaging device; a stereoscopic display device; and a control unit configured to control display of the display device on the basis of a detection value indicating a focus state of a lens acquired from the imaging device, and a captured image signal for a left eye and a captured image signal for a right eye acquired from the imaging device.

Advantageous Effects of Invention

According to the present disclosure as described above, it is possible to alleviate discomfort that the user experiences during operation of autofocus.

Note that the effects described above are not necessarily limitative. With or in the place of the above effects, there may be achieved any one of the effects described in this specification or other effects that may be grasped from this specification.

MODES FOR CARRYING OUT THE INVENTION

Figure 1:
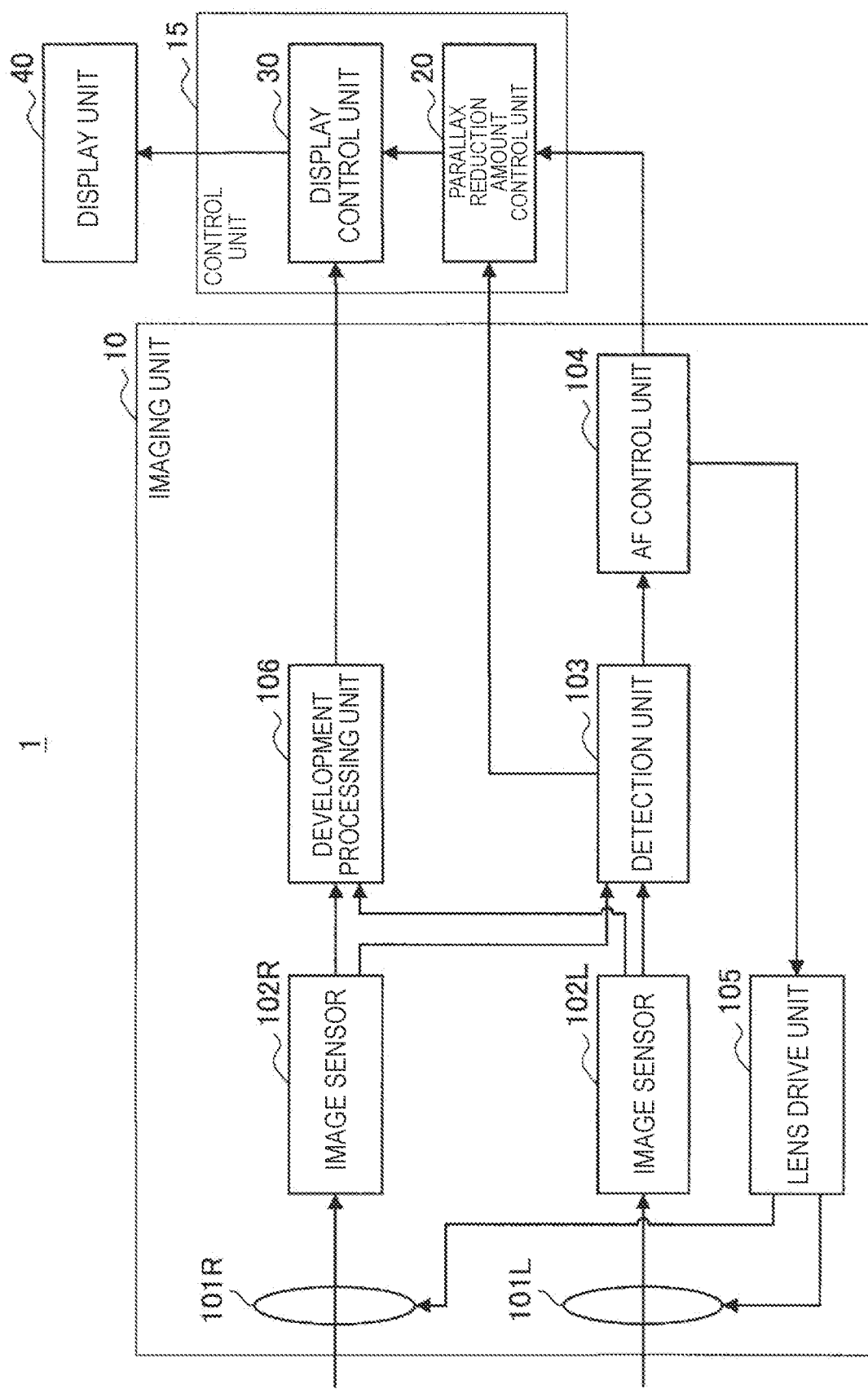
FIG. 1 is a block diagram of an example configuration of an information processing apparatus 1 according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be given in the following order.
<<1. Example Configuration>>
  <1-1. General Configuration>
  <1-2. Display Control Unit>
<<2. Example Operation>>
<<3. Modifications>>
  <3-1. Modification 1>
  <3-2. Modification 2>
  <3-3. Modification 3>
  <3-4. Modification 4>
<<4. Hardware Configuration Example>>
<<5. Conclusion>>

1. Example Configuration

<1-1. General Configuration>

First, an example configuration according to an embodiment of the present disclosure will be described with reference to FIG. 1. FIG. 1 is a block diagram of an example configuration of an information processing apparatus 1 according to an embodiment of the present disclosure. The information processing apparatus 1 according to the present embodiment is an information processing apparatus that displays a stereoscopically viewable image on the basis of imaging.

As illustrated in FIG. 1, the information processing apparatus 1 according to the present embodiment includes an imaging unit 10, a control unit 15, and a display unit 40.
(Imaging Unit)

The imaging unit 10 is a stereoscopic imaging unit (imaging device) and acquires two image signals (a captured image signal for the left eye, and a captured image signal for the right eye) on the basis of imaging. As illustrated in FIG. 1, the imaging unit 10 according to the present embodiment includes lenses 101L and 101R, image sensors 102L and 102R, a detection unit 103, an AF control unit 104, a lens drive unit 105, and a development processing unit 106.

The lenses 101L and 101R are focus lenses that are moved (driven) by the lens drive unit 105 and used for focus adjustment in the imaging unit 10. The lenses 101L and 101R adjust the focus on the subject, collect light from the focus position, and deliver the light to the image sensors 102L and 102R.

The image sensors 102L and 102R are image sensors that are arranged laterally and have a plurality of pixels. The image sensors 102L and 102R photoelectrically convert incident light and output a pixel signal for each pixel. Here, the image sensor 102L performs imaging for the left eye, and the image sensor 102R performs imaging for the right eye.

The detection unit 103 acquires an AF detection value (hereinafter, may also be referred to simply as a detection value) indicating the focus state of the lens on the basis of the pixel signals acquired from at least one of the image sensor 102L or 102R. The type of detection value and the method for acquiring the detection value by the detection unit 103 depend on the autofocus method associated with the imaging unit 10. The detection unit 103 according to the present embodiment acquires a larger detection value as the degree of focus of the lens is larger.

The AF method associated with the imaging unit 10 may be, for example, a contrast AF method involving performing focus adjustment so as to increase the contrast of the image obtained by imaging. In this case, for example, the detection unit 103 may specify an absolute difference between horizontally adjacent pixel levels (pixel values) for each pixel and may acquire, as the detection value associated with the image sensor, the maximum value of the absolute differences specified in each image sensor.

The AF control unit 104 controls autofocus (AF) on the basis of the detection value obtained by the detection unit 103. The AF control unit 104 specifies, as lens movement parameters, the direction (e.g., forward or backward direction) in which the lenses 101L and 101R are moved and the amount of movement and outputs lens drive signals including the lens movement parameters to a lens drive unit 105. Note that the AF control unit 104 may independently specify the lens movement parameters associated with each of the lenses 101L and 101R according to the configuration of the lens drive unit 105, or may specify the lens movement parameters common to both the lenses 101L and 101R. In addition, the AF control unit 104 provides the information (e.g., lens movement start time, lens movement speed) related to autofocus control to the control unit 15.

The lens drive unit 105 is a unit configured to move the lenses 101L and 101R on the basis of the lens drive signals and is realized by, for example, a motor. The lens drive unit 105 may independently move the lenses 101L and 101R, or may move the lenses 101L and 101R on the basis of the lens movement parameters common to both the lenses 101L and 101R.

The development processing unit 106 performs development processing on the basis of the pixel signals acquired from the image sensors 102L and 102R and acquires image signals (a captured image signal for the left eye, and a captured image signal for the right eye) associated with the image sensors 102L and 102R. The development processing performed by the development processing unit 106 may also include, for example, demosaic processing. In addition, the development processing unit 106 may further perform processing, such as black level correction processing, gamma correction processing, and white balance correction processing. The development processing unit 106 outputs, to the control unit 15 described below, the captured image signal for the left eye associated with the image sensor 102L and the captured image signal for the right eye associated with the image sensor 102R.
(Control Unit)

The control unit 15 controls each unit of the information processing apparatus 1. Moreover, as illustrated in FIG. 1, the control unit 15 also functions as a parallax reduction amount control unit 20 and a display control unit 30.

Figure 2:
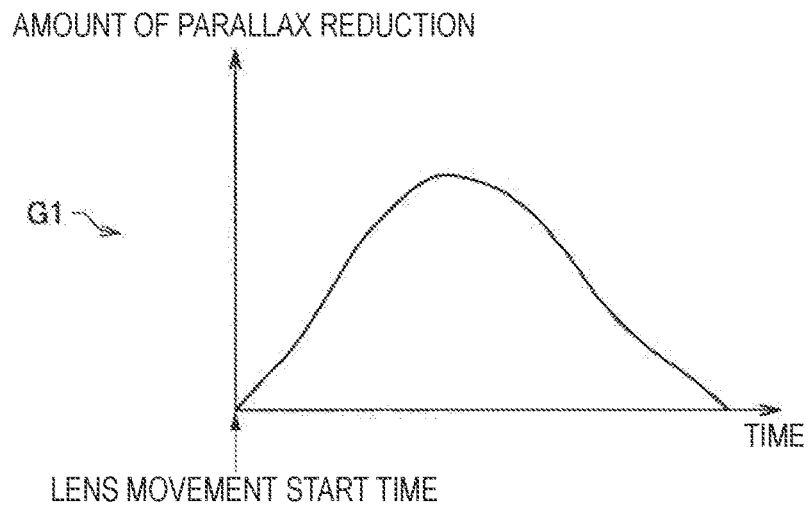
FIG. 2 illustrates explanatory graphs for describing example control of the amount of parallax reduction by a parallax reduction amount control unit 20.
Figure 2:
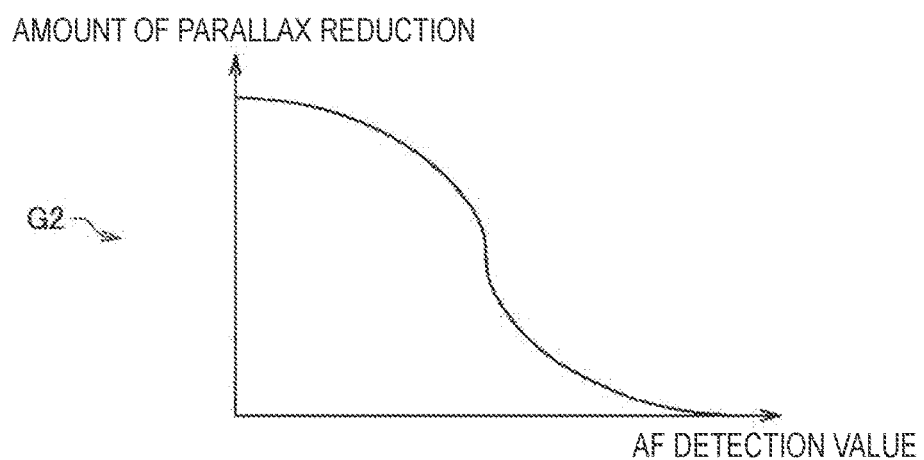
Figure 2:
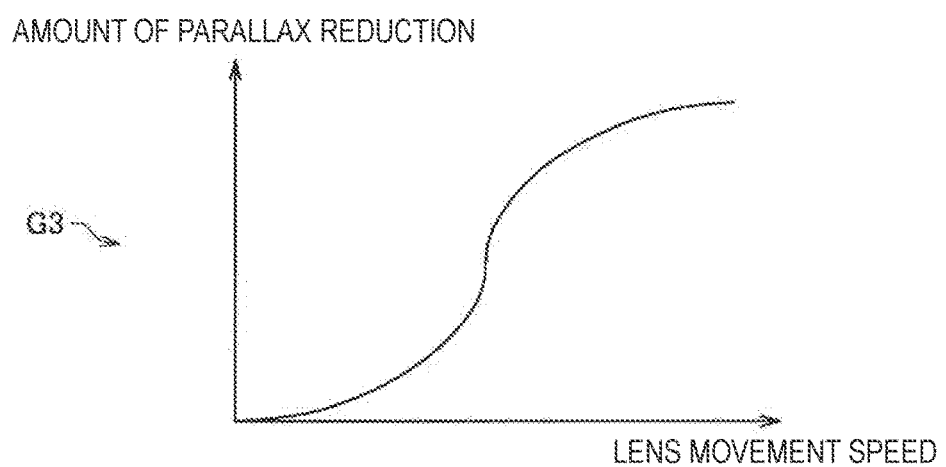

The parallax reduction amount control unit 20 controls the amount of parallax reduction, which indicates the degree at which parallax associated with display is to be reduced, on the basis of the detection value acquired by the detection unit 103. The parallax reduction amount control unit 20 may control the amount of parallax reduction directly on the basis of the detection value, or may control the amount of parallax reduction on the basis of the information associated with autofocus control performed on the basis of the detection value. FIG. 2 illustrates explanatory graphs for describing example control of the amount of parallax reduction by the parallax reduction amount control unit 20.

As illustrated in graph G1 of FIG. 2, the parallax reduction amount control unit 20 may control the amount of parallax reduction on the basis of the lens movement start time (AF operation start time) in autofocus control. In this case, as illustrated in graph G1 of FIG. 2 the parallax reduction amount control unit 20 may control the amount of parallax reduction such that the amount of parallax reduction increases for a predetermined time from the lens movement start time and decreases after the predetermined time. According to this configuration, during AF operation, the display control unit 30 described below may slowly perform display control processing, which alleviates discomfort that the user experiences.

In addition, as illustrated in graph G2 of FIG. 2, the parallax reduction amount control unit 20 may control the amount of parallax reduction on the basis of the detection value acquired by the detection unit 103. In this case, as illustrated in graph G2 of FIG. 2, the parallax reduction amount control unit 20 may perform control such that the amount of parallax reduction decreases as the detection value increases. According to this configuration, in the case of a small detection value, the subject is out of focus (the degree of focus is low), and AF is in operation. Thus, a large amount of parallax reduction can alleviate discomfort that the user experiences by means of display control of the display control unit 30 described below. Moreover, in the case of a large detection value, the subject is in focus (the degree of focus is high), and AF is out of operation. Thus, a small amount of parallax reduction tends to cause display of comfortably and stereoscopically viewable images.

In addition, as illustrated in graph G3 of FIG. 2, the parallax reduction amount control unit 20 may control the amount of parallax reduction on the basis of the lens movement speed (the amount of movement of the lens per predetermined time) in autofocus control. In this case, as illustrated in graph G3 of FIG. 2, the parallax reduction amount control unit 20 may perform control such that the amount of parallax reduction increases as the lens movement speed increases. According to this configuration, the optimum lens position is being searched when the lens movement speed is high. Thus, a large amount of parallax reduction can alleviate discomfort that the user experiences by means of display control of the display control unit 30 described below. Moreover, the subject is in focus when the lens movement speed is low. Thus, a small amount of parallax reduction tends to cause display of comfortably and stereoscopically viewable images.

Note that the control of the amount of parallax reduction by the parallax reduction amount control unit 20 is not limited to the example described above. For example, the parallax reduction amount control unit 20 may control the amount of parallax reduction on the basis of the captured image signal for the left eye and the captured image signal for the right eye. For example, the parallax reduction amount control unit 20 may perform control such that the amount of parallax reduction increases when a subject including a steep edge is determined to be captured on the basis of edge detection processing on the images obtained from the captured image signal for the left eye and the captured image signal for the right eye. In addition, the parallax reduction amount control unit 20 may perform control such that the amount of parallax reduction is small in the case of a captured image having a low contrast. Moreover, the parallax reduction amount control unit 20 may control the amount of parallax reduction by combining several types of control processing on the amount of parallax reduction described above. The values of the amount of parallax reduction according to arithmetic expression, imaging device, user, or the like may be stored in advance in a storage unit (not shown). The parallax reduction amount control unit 20 may control the amount of parallax reduction by selecting a suitable value from the storage unit according to arithmetic expression, imaging device, user, or the like. Alternatively, the amount of parallax reduction may be inputted (set) by the user during the use of the imaging unit 10, and the parallax reduction amount control unit 20 may control the amount of parallax reduction on the basis of the user's input.

The display control unit 30 controls display on the display unit 40 on the basis of the captured image signal for the left eye and the captured image signal for the right eye acquired from the imaging unit 10 and the amount of parallax reduction controlled on the basis of the detection value. The display control of the display control unit 30 will be described below in detail with reference to FIGS. 3 to 12. The display control unit 30 controls display so as to alleviate discomfort that the user experiences during autofocus operation in the imaging unit 10.

(Imaging Unit)

The display unit 40 is a stereoscopic display unit (display device). The display unit 40 is controlled by the display control unit 30 and displays a display image for the left eye and a display image for the right eye.

<1-2. Display Control Unit>

Figure 3:
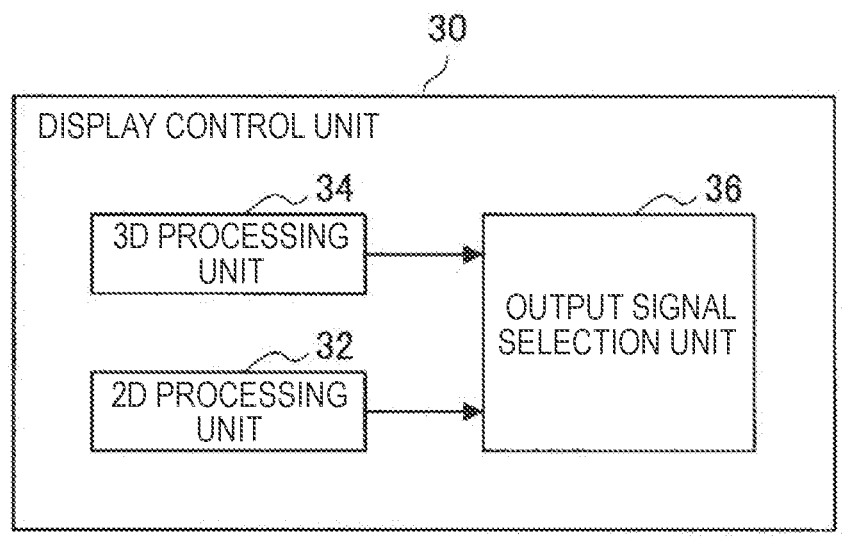
FIG. 3 is a block diagram of an example configuration of a display control unit 30 according to the embodiment.

The general configuration of the information processing apparatus 1 according to the present embodiment is described above. Next, the display control unit 30 will be described in detail with reference to FIGS. 3 to 12. FIG. 3 is a block diagram of an example configuration of the display control unit 30 according to the present embodiment.

As illustrated in FIG. 3, the display control unit 30 has a 2D processing unit 32, a 3D processing unit 34, and an output signal selection unit 36. The 2D processing unit 32 and the 3D processing unit 34 each output an image signal (output image signal) on the basis of the captured image signal for the left eye and the captured image signal for the right eye acquired from the imaging unit 10 and the amount of parallax reduction. Moreover, the output signal selection unit 36 selects which signal is used for display control, the output image signal outputted from the 2D processing unit 32, or the output image signal outputted from the 3D processing unit 34. Specifically, depending on selection of the output signal selection unit 36, there are a case where display is controlled by the output image signal from the 2D processing unit 32 and a case where display is controlled by the output image signal from the 3D processing unit 34. Hereinafter, the function of each of the 2D processing unit 32, the 3D processing unit 34, and the output signal selection unit 36 will be described in more detail.

The 2D processing unit 32 may output, for example, two image signals having no binocular disparity (cannot be stereoscopically viewed) on the basis of the captured image signal for the left eye and the captured image signal for the right eye acquired from the imaging unit 10 and the amount of parallax reduction. Hereinafter, some example configurations of the 2D processing unit 32 will be described with reference to FIGS. 4 to 7.

(First Example Configuration of 2D Processing Unit)

Figure 4:
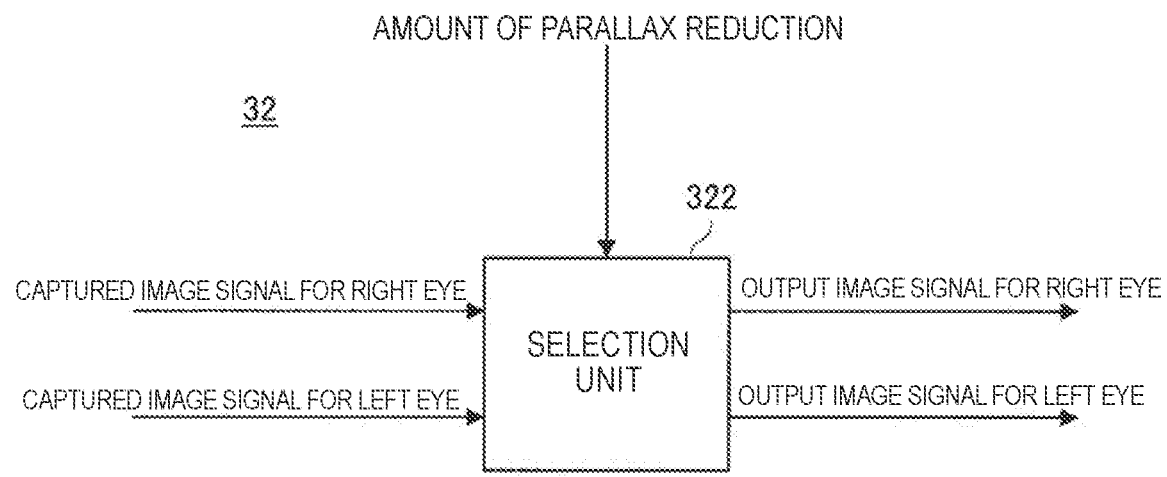
FIG. 4 is an explanatory diagram illustrating a first example configuration of a 2D processing unit 32 according to the embodiment.

FIG. 4 is an explanatory diagram illustrating a first example configuration of a 2D processing unit 32 illustrated in FIG. 3. The 2D processing unit 32 illustrated in FIG. 4 includes a selection unit 322. The selection unit 322 receives input about the captured image signal for the left eye associated with the image sensor 102L, the captured image signal for the right eye associated with the image sensor 102R, and the amount of parallax reduction. Moreover, the selection unit 322 outputs the output image signal for the left eye and the output image signal for the right eye on the basis of the forgoing input.

For example, the selection unit 322 may output the captured image signal for the left eye as the output image signal for the left eye, and select one of the captured image signal for the left eye and the captured image signal for the right eye on the basis of the amount of parallax reduction and output the selected signal as the output image signal for the right eye. For example, the selection unit 322 may output the captured image signal for the left eye as the output image signal for the right eye in the case where the amount of parallax reduction is larger than a predetermined threshold, and output the captured image signal for the right eye as the output image signal for the right eye in the case where the amount of parallax reduction is smaller than or equal to a predetermined threshold. Note that the predetermined threshold may be 0.

Figure 5:
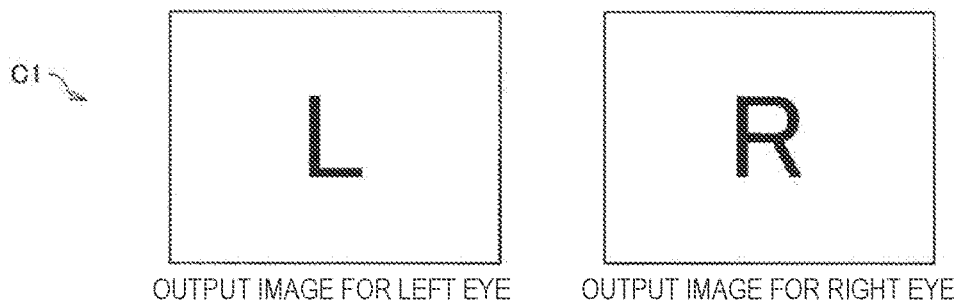
FIG. 5 is an explanatory diagram for describing output images obtained from output image signals of a selection unit 322 according to the embodiment.
Figure 5:
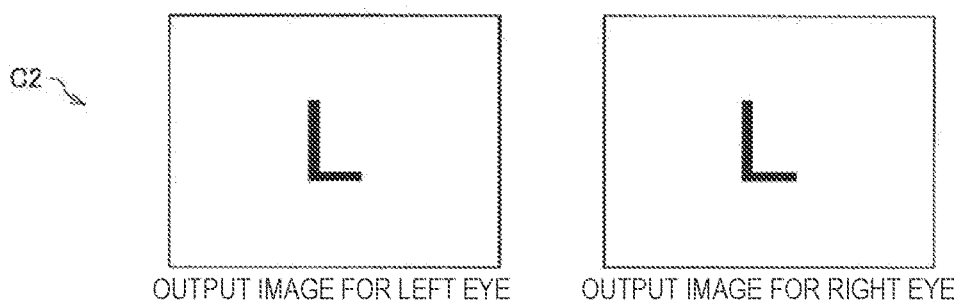

FIG. 5 is an explanatory diagram for describing output images obtained from output image signals of the selection unit 322. The state C1 illustrated in FIG. 5 shows output images in the case where the amount of parallax reduction is smaller than or equal to a predetermined threshold. In the state C1 illustrated in FIG. 5, the output image for the left eye is a captured image for the left eye obtained from the captured image signal for the left eye, and the output image for the right eye is a captured image for the right eye obtained from the captured image signal for the right eye.

On the other hand, the state C2 illustrated in FIG. 5 shows output images in the case where the amount of parallax reduction is larger than a predetermined threshold. In the state C2 illustrated in FIG. 5, the output image for the left eye and the output image for the right eye both are captured images for the left eye obtained from the captured image signal for the left eye. Specifically, the display control unit 30 may control display such that the display image for the left eye and the display image for the right eye in the display are same images in the case where the amount of parallax reduction is larger than a predetermined threshold. According to this configuration, an image having no parallax is presented to the user, and thus discomfort that the user experiences due to stereopsis of an unfocused image is suppressed.

Note that an example in which the selection unit 322 performs selection associated with the output image signal for the right eye is described above, but the present embodiment of the present disclosure is not limited to this example. Specifically, the 2D processing unit 32 may be configured such that the relationship between the captured image signal for the left eye and the captured image signal for the right eye in the 2D processing unit 32 and the output image signal for the left eye and the output image signal for the right eye is reversed.

For example, the selection unit 322 may perform selection associated with the output image signal for the left eye. In this example, the selection unit 322 may output the captured image signal for the right eye as the output image signal for the left eye and the output image signal for the right eye in the case where the amount of parallax reduction is larger than a predetermined threshold. Note that which one of selection associated with the output image signal for the right eye and selection associated with the output image signal for the left eye is performed by the selection unit 322 may be determined by the user or may be determined on the basis of the information about the dominant eye of the user. In the case where determination is made on the basis of the information about the dominant eye of the user, the selection unit 322 may perform selection associated with the output image signal corresponding to the non-dominant eye.

(Second Example Configuration of 2D Processing Unit)

Figure 6:
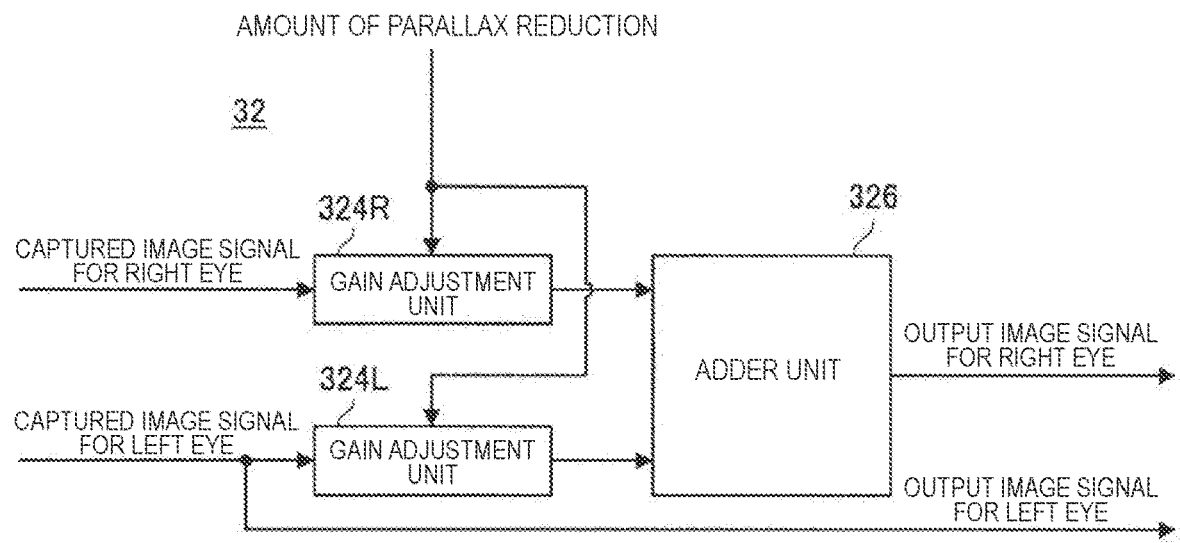
FIG. 6 is an explanatory diagram illustrating a second example configuration of the 2D processing unit 32 according to the embodiment.

FIG. 6 is an explanatory diagram illustrating a second example configuration of the 2D processing unit 32 illustrated in FIG. 3. The 2D processing unit 32 illustrated in FIG. 6 includes gain adjustment units 324L and 324R and an adder unit 326. The 2D processing unit 32 illustrated in FIG. 6 outputs the captured image signal for the left eye as the output image signal for the left eye. Moreover, the 2D processing unit 32 illustrated in FIG. 6 combines the captured image signal for the left eye and the captured image signal for the right eye in accordance with the amount of parallax reduction and outputs the resulting signal as the output image signal for the right eye.

The gain adjustment units 324L and 324R respectively multiply the captured image signal for the left eye and the captured image signal for the right eye by a gain corresponding to the amount of parallax reduction. For example, given that the gain associated with the gain adjustment unit 324R is $\alpha$, the gain associated with the gain adjustment unit 324L may be $1-\alpha$. Alternatively, the $\alpha$-value may be set to 1 in the case where the amount of parallax reduction is 0, and the $\alpha$-value may be set so as to approach 0 as the amount of parallax reduction increases. Note that, in the case where $\alpha$ is 0, the display image for the left eye and the display image for the right eye in the display may be the same images.

The adder unit 326 adds (combines) the outputs from the gain adjustment units 324L and 324R, and outputs the resulting signal as the output image signal for the right eye. According to this configuration, the output image signal for the right eye is a signal obtained by combining (what is called alpha blending) the captured image signal for the left eye and the captured image signal for the right eye. In other words, the display control unit 30 may cause display of an image formed by combining the captured image for the left eye obtained from the captured image signal for the left eye and the captured image for the right eye obtained from the captured image signal for the right eye, in accordance with the amount of parallax reduction. According to this configuration, the displayed image gradually changes in accordance with the amount of parallax reduction. The user is thus unlikely to experience unpleasant sensation.

Note that, like the 2D processing unit 32 described with reference to FIG. 4, the 2D processing unit 32 illustrated in FIG. 6 may be configured such that the relationship between the captured image signal for the left eye and the captured image signal for the right eye and the output image signal for the left eye and the output image signal for the right eye is reversed.

(Third Example Configuration of 2D Processing Unit)

Figure 7:
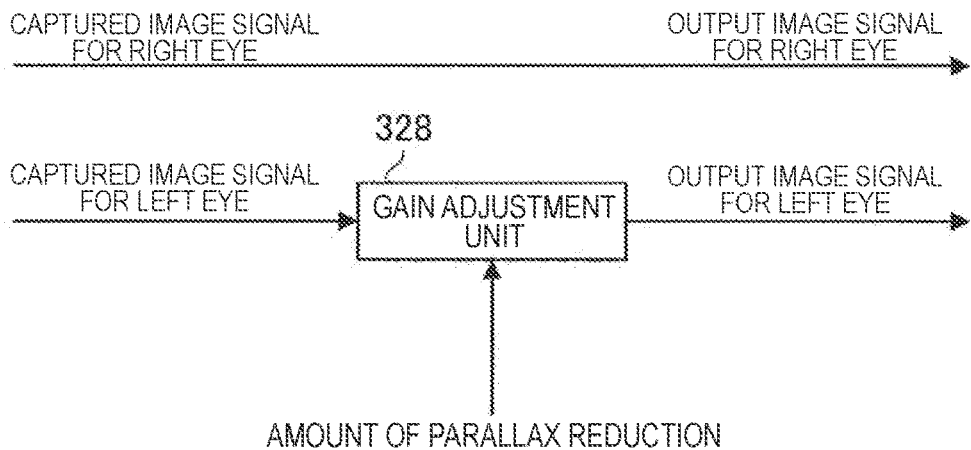
FIG. 7 is an explanatory diagram illustrating a third example configuration of the 2D processing unit 32 according to the embodiment.

FIG. 7 is an explanatory diagram illustrating a third example configuration of the 2D processing unit 32 illustrated in FIG. 3. The 2D processing unit 32 illustrated in FIG. 7 includes a gain adjustment unit 328. The 2D processing unit 32 illustrated in FIG. 7 outputs the captured image signal for the right eye as the output image signal for the right eye. Moreover, in the 2D processing unit 32 illustrated in FIG. 7, the captured image signal for the left eye is multiplied by a gain corresponding to the amount of parallax reduction, and the resulting signal is outputted as the output image signal for the left eye.

The gain adjustment unit 328 multiplies the captured image signal for the left eye by a gain corresponding to the amount of parallax reduction and outputs the resulting signal as the output image signal for the left eye. Given that the gain associated with the gain adjustment unit 328 is α, the α-value may be set to 1 in the case where the amount of parallax reduction is 0, and the α-value may be set so as to approach 0 as the amount of parallax reduction increases. In other words, the display control unit 30 may cause display of an image formed by reducing the pixel level of the captured image for the left eye obtained from the captured image signal for the left eye, in accordance with the amount of parallax reduction. Note that, in the case where α is 0, the user may perceive only the display image for the right eye.

Note that, like the 2D processing unit 32 described with reference to FIG. 4, the 2D processing unit 32 illustrated in FIG. 7 may be configured such that the relationship between the captured image signal for the left eye and the captured image signal for the right eye and the output image signal for the left eye and the output image signal for the right eye is reversed. In other words, the display control unit 30 may cause display of an image formed by reducing the pixel level of the captured image for the right eye obtained from the captured image signal for the right eye, in accordance with the amount of parallax reduction. Furthermore, the display control unit 30 may cause display of an image formed by reducing the pixel levels of both the captured image for the left eye and the captured image for the right eye, in accordance with the amount of parallax reduction.

Some example configurations of the 2D processing unit 32 are described above. Next, the 3D processing unit 34 illustrated in FIG. 3 will be described. The 3D processing unit 34 performs, for example, processing on both the captured image for the left eye and the captured image for the right eye in order to reduce user's discomfort in stereoscopic display. Moreover, the 3D processing unit 34 may output, for example, two image signals having binocular disparity (stereoscopically viewable-image signals) on the basis of the captured image signals obtained from the imaging unit 10 and the amount of parallax reduction. Hereinafter, some example configurations of the 3D processing unit 34 will be described with reference to FIGS. 8 to 12.

(First Example Configuration of 3D Processing Unit)

Figure 8:
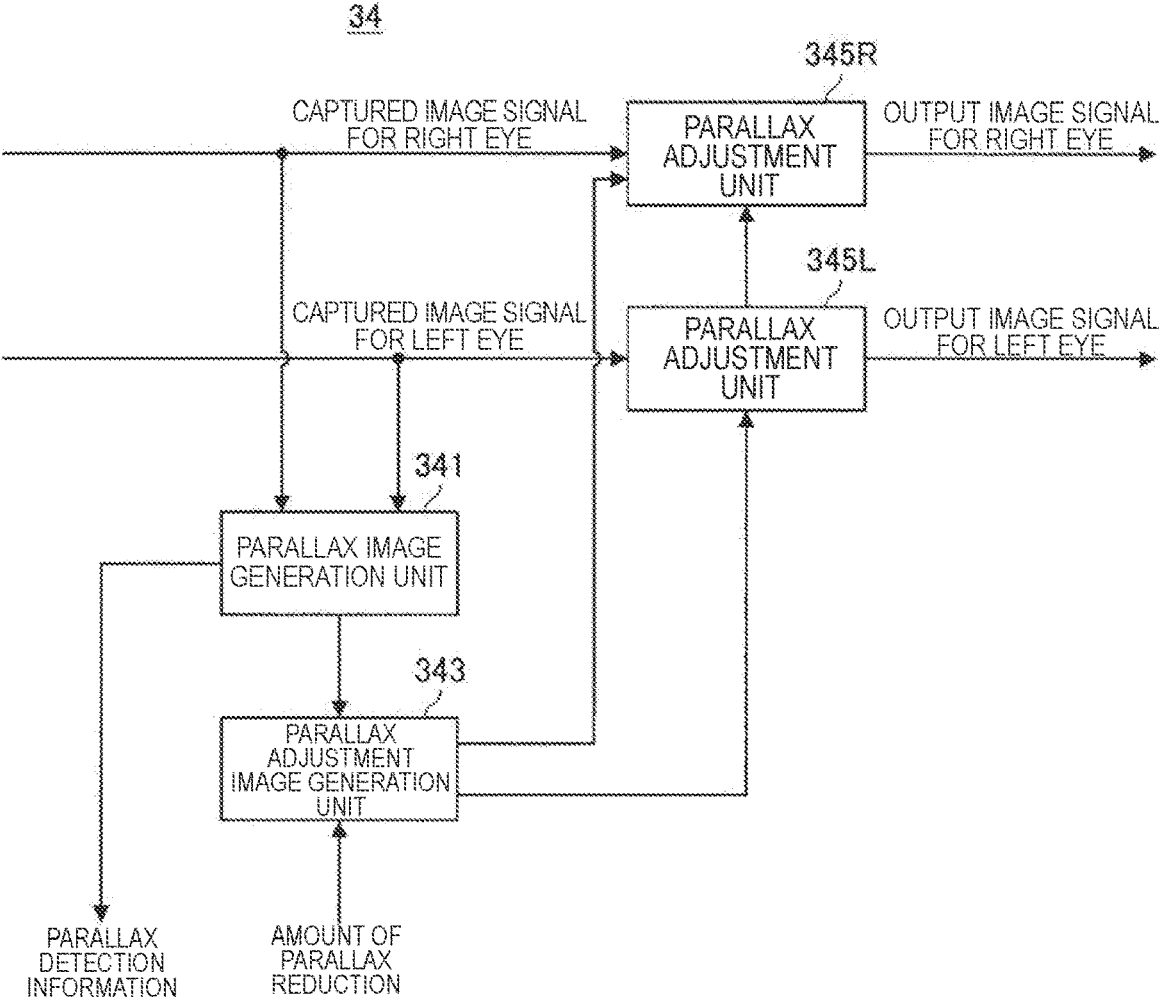
FIG. 8 is an explanatory diagram illustrating a first example configuration of a 3D processing unit 34 according to the embodiment.

FIG. 8 is an explanatory diagram illustrating a first example configuration of the 3D processing unit 34 illustrated in FIG. 3. The 3D processing unit 34 illustrated in FIG. 8 includes a parallax image generation unit 341, a parallax adjustment image generation unit 343, and parallax adjustment units 345L and 345R. The display control unit 30 having the 3D processing unit 34 illustrated in FIG. 8 may control display by performing parallax adjustment processing on the captured image for the left eye and the captured image for the right eye so as to reduce parallax associated with display on the basis of matching between the captured image for the left eye obtained from the captured image signal for the left eye and the captured image for the right eye obtained from the captured image signal for the right eye.

The parallax image generation unit 341 generates a parallax image signal indicating parallax at each position in each image by matching between the captured image for the left eye obtained from the captured image signal for the left eye and the captured image for the right eye obtained from the captured image signal for the right eye.

The parallax image generation unit 341 may specify, for example, the amount of displacement (parallax) between the pixels of the captured image for the left eye and the corresponding pixels of the captured image for the right eye by means of block matching and generate a parallax image signal associated with a parallax image showing a map of parallax at each point. Moreover, the parallax image generation unit 341 may output, as parallax detection information, the value obtained as follows: taking absolute differences between block units each including a plurality of pixels in block matching; summing these absolute differences; and producing the sum of the summed absolute differences in the entire image. The parallax detection information is an indication of the precision of parallax detection or parallax reduction in the 3D processing unit and is used for selection performed by the output signal selection unit 36. Note that, in the case where the amount of the parallax detection information specified as described above is large, there is a high possibility that mismatching occurs for the reason that occlusion regions are present between left and right images or for other reasons. Thus, there is a risk of low precision of parallax detection. Moreover, if the precision of parallax detection is low, the precision of parallax reduction (parallax adjustment) described below may also be low.

On the basis of the parallax image signal and the amount of parallax reduction, the parallax adjustment image generation unit 343 generates a parallax adjustment image signal associated with a parallax adjustment image for reducing parallax at each position. For example, given that the amount of parallax in the parallax image at a position (x, y) is d(x, y), the output c(x, y) of the parallax adjustment image is represented by the following formula (1).

$$c(x,y)=(d(x,y)-d(x,y)/a)/2 \qquad (1)$$

Note that, in the formula (1), a is a constant of 1 or larger in accordance with the amount of parallax reduction. For example, the a-value may be set so as to increase as the amount of parallax reduction increases.

The parallax adjustment units 345L and 345R perform parallax adjustment processing, which reduces parallax, on the captured image signal for the left eye and the captured image signal for the right eye on the basis of the parallax adjustment image signal, and output the output image signal for the left eye and the output image signal for the right eye, respectively.

Figure 9:
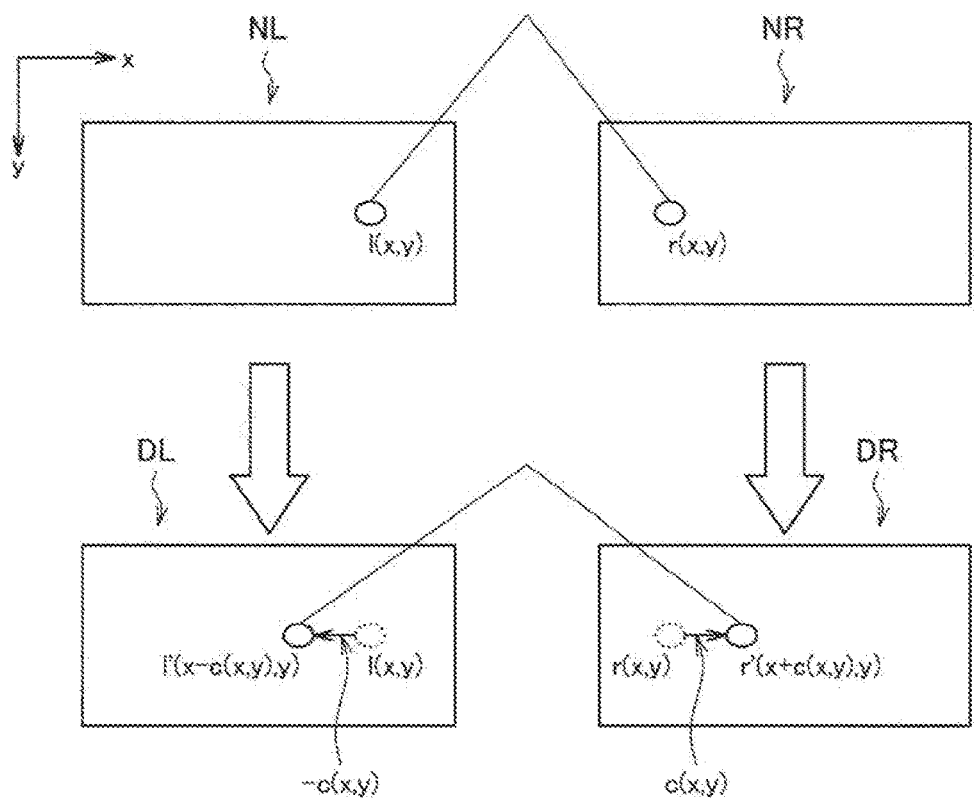
FIG. 9 is a schematic diagram for describing parallax adjustment processing performed by parallax adjustment units 345L and 345R according to the embodiment.

FIG. 9 is a schematic diagram for describing parallax adjustment processing performed by the parallax adjustment units 345L and 345R. The parallax adjustment units 345L and 345R shift each pixel position horizontally (in the x-axis direction) on the basis of the output c(x, y) of the parallax adjustment image.

For example, pixel l(x, y) in a captured image NL for the left eye illustrated in FIG. 9 is shifted by −c(x, y) in the x-axis direction. Specifically, as illustrated in FIG. 9, the value of pixel l'(x−c(x, y), y) of a left image DL in the output image signal for the left eye corresponds to the value of pixel l(x, y) in a captured image NL for the left eye. Similarly, as illustrated in FIG. 9, the value of pixel r'(x+c(x, y), y) of the left image DR in the output image signal for the right eye corresponds to the value of pixel r(x, y) in a captured image NR for the right eye. Note that, in FIG. 9, pixel l(x, y) in the captured image NL for the left eye and pixel r(x, y) in the captured image NR for the right eye are pixels matched (associated with each other) by the parallax image generation unit 341.

The parallax adjustment processing as described above may reduce the parallax in each pixel and alleviate the burden on the user associated with stereopsis.

(Second Example Configuration of 3D Processing Unit)

Figure 10:
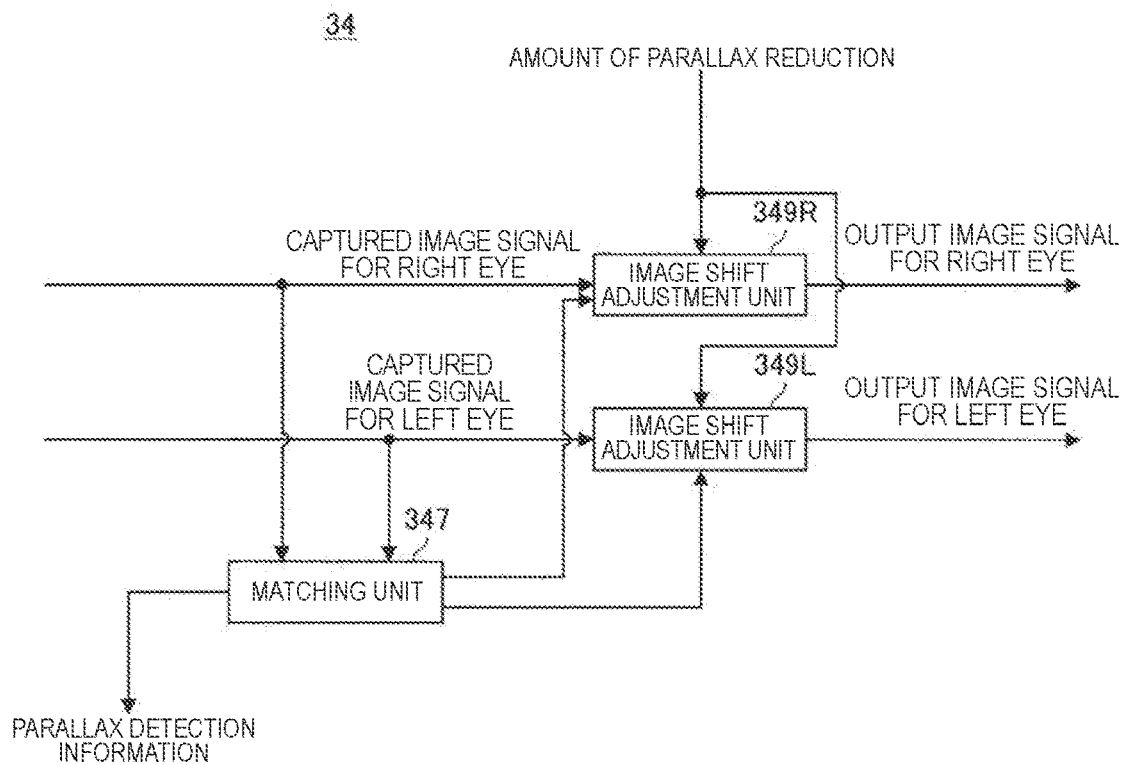
FIG. 10 is an explanatory diagram illustrating a second example configuration of the 3D processing unit 34 according to the embodiment.

FIG. 10 is an explanatory diagram illustrating a second example configuration of the 3D processing unit 34 illustrated in FIG. 3. The 3D processing unit 34 illustrated in FIG. 10 includes a matching unit 347 and image shift adjustment units 349L and 349R.

The display control unit 30 having the 3D processing unit 34 illustrated in FIG. 10 may control display by performing parallax adjustment processing on the captured image for the left eye and the captured image for the right eye so as to reduce parallax associated with the display on the basis of matching between the captured image for the left eye and the captured image for the right eye. The 3D processing unit 34 described with reference to FIG. 8 performs parallax adjustment processing on the basis of matching at each position (each pixel) in the images, while the 3D processing unit 34 illustrated in FIG. 10 performs parallax adjustment processing on the basis of matching over the entire image. According to this configuration, the amount of calculation is reduced.

The matching unit 347 specifies the amount of shift in entire image between the captured image for the left eye and the captured image for the right eye by matching over the entire image. For example, the matching unit 347 may calculate absolute differences while horizontally shifting the captured image for the left eye and the captured image for the right eye, and specify, as the amount of shift in entire image between the captured image for the left eye and the captured image for the right eye, the amount of shift with which the sum of the absolute differences in the entire image is smallest. Moreover, the matching unit 347 may output the above-described sum of the absolute differences in the entire image as the parallax detection information.

The image shift adjustment units 349L and 349R perform parallax adjustment processing on the captured image signal for the left eye and the captured image signal for the right eye on the basis of the amount of shift specified by the matching unit 347 and the amount of parallax reduction. For example, the image shift adjustment units 349L and 349R may perform parallax adjustment processing by specifying the amount of parallax adjustment on the basis of the amount of shift and the amount of parallax adjustment and shifting the entire captured image for the left eye and the entire captured image for the right eye by the specified amount of parallax adjustment. For example, given that the amount of shift is d, the amount of parallax adjustment c is represented by the following formula (2).

$$c = (d - d/a)/2 \quad (2)$$

Note that, in the formula (2), a is a constant of 1 or larger in accordance with the amount of parallax reduction, and the a-value may be set so as to increase as the amount of parallax reduction increases.

(Third Example Configuration of 3D Processing Unit)

Figure 11:
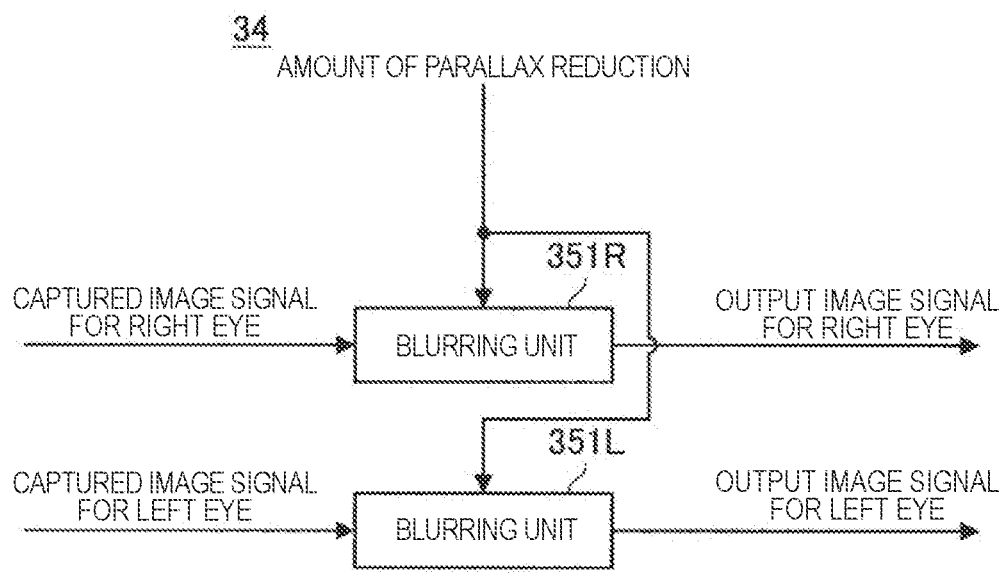
FIG. 11 is an explanatory diagram illustrating a third example configuration of the 3D processing unit 34 according to the embodiment.

FIG. 11 is an explanatory diagram illustrating a third example configuration of the 3D processing unit 34 illustrated in FIG. 3. The 3D processing unit 34 illustrated in FIG. 11 includes blurring units 351L and 351R.

The blurring units 351L and 351R respectively perform blur processing on the captured image signal for the left eye and the captured image signal for the right eye in accordance with the amount of parallax reduction, and respectively output the output image signal for the left eye and the output image signal for the right eye.

For example, the blurring units 351L and 351R may perform blur processing such that the degree of blurring increases as the amount of parallax reduction increases. The blurring units 351L and 351R may each include, for example, a Gaussian blur filter. In this case, the variance in the Gaussian function may be set to a larger value as the amount of parallax reduction is larger.

During AF operation, a large change in the degree of blurring of the image due to lens movement tends to make the user experience discomfort. According to the foregoing configuration, during AF operation, display control is performed such that an increase in change in the degree of blurring is suppressed by blurring the displayed image (producing the blurred image) in accordance with the amount of parallax reduction. Such display control can alleviate discomfort that the user experiences.

(Fourth Example Configuration of 3D Processing Unit)

Figure 12:
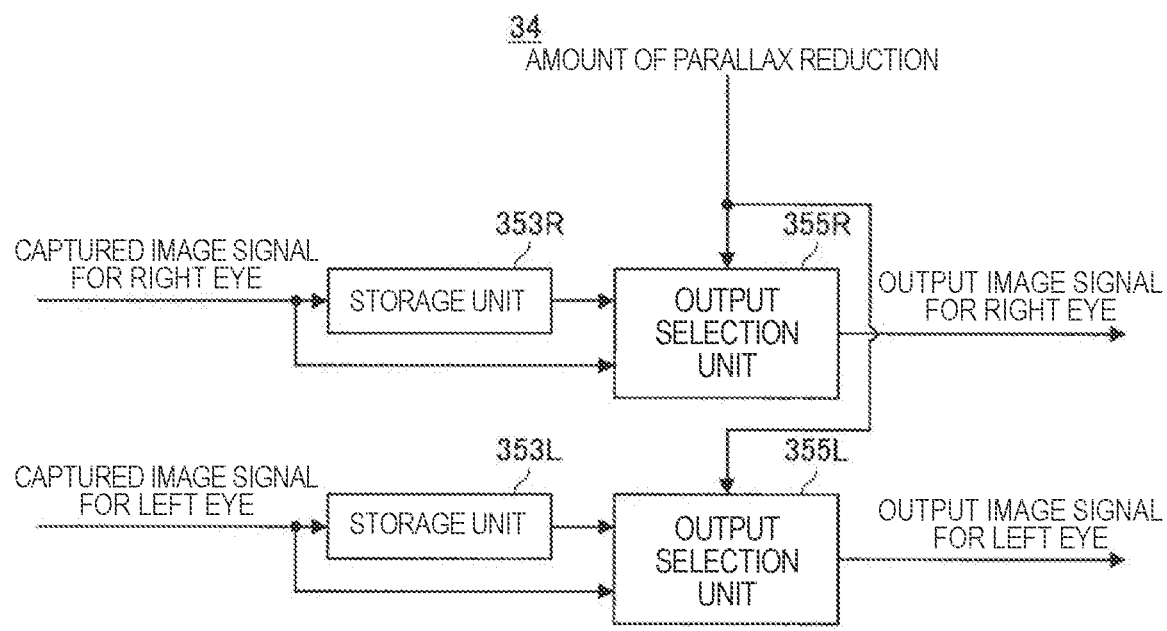
FIG. 12 is an explanatory diagram illustrating a fourth example configuration of the 3D processing unit 34 according to the embodiment.

FIG. 12 is an explanatory diagram illustrating a fourth example configuration of the 3D processing unit 34 illustrated in FIG. 3. The 3D processing unit 34 illustrated in FIG. 12 includes storage units 353L and 353R and output selection units 355L and 355R.

The storage units 353L and 353R respectively store the captured image signal for the left eye and the captured image signal for the right eye. The storage units 353L and 353R may respectively store, for example, a predetermined time of the captured image signal for the left eye and a predetermined time of the captured image signal for the right eye.

The output selection units 355L and 355R respectively output the output image signal for the left eye and the output image signal for the right eye on the basis of the amount of parallax reduction. In the case where, for example, the amount of parallax reduction is larger than a predetermined threshold, the output selection units 355L and 355R may respectively output, as the output image signal for the left eye and the output image signal for the right eye, the captured image signal for the left eye and the captured image signal for the right eye that are stored in the storage units 353L and 353R. Moreover, in the case where, for example, the amount of parallax reduction is smaller than or equal to a predetermined threshold, the output selection units 355L and 355R may respectively output the current captured image signal for the left eye and the current captured image signal for the right eye as the output image signal for the left eye and the output image signal for the right eye.

In the case where the output selection units 355L and 355R respectively output, as the output image signal for the left eye and the output image signal for the right eye, the captured image signal for the left eye and the captured image signal for the right eye that are stored in the storage units 353L and 353R, the captured image signal for the left eye and the captured image signal for the right eye may be captured image signals based on imaging just before start of movement of the lens in AF control of the AF control unit 104.

According to this configuration, an image having a degree of blurring that greatly changes with lens movement during AF operation is not displayed, and an image obtained from the captured image signal for the left eye and the captured image signal for the right eye based on imaging just before start of movement of the lens is displayed. Such image display can alleviate discomfort that the user experiences.

(Output Signal Selection Unit)

The output signal selection unit 36 selects which signal is used for display control, the output image signal outputted from the 2D processing unit 32, or the output image signal outputted from the 3D processing unit 34. The output signal selection unit 36 may control display by performing selection, for example, in accordance with the user's input inputted through an operation unit (not shown).

Moreover, as described with reference to FIG. 8 and FIG. 10, in the case where the 3D processing unit 34 is configured to output parallax detection information and perform parallax adjustment processing, the output signal selection unit 36 may control display by performing the foregoing selection in accordance with the parallax detection information. For example, in the case where the amount of the parallax detection information is large, there is a risk of low precision of parallax detection or parallax reduction. Thus, the output signal selection unit 36 may select the output image signal from the 2D processing unit 32, and the display control unit 30 may perform display control on the basis of processing performed by the 2D processing unit 32. Meanwhile, in the case where the amount of the parallax detection information is small, the output signal selection unit 36 may select the output image signal from the 3D processing unit 34, and the display control unit 30 may perform display control on the basis of parallax adjustment processing performed by the 3D processing unit 34.

Note that, if control is performed so as to provide image display different from normal during operation of autofocus as a result of selection of the output signal selection unit 36, the display control unit 30 may cause display of a notice indicating that display control processing for alleviating discomfort in stereopsis is performed. For example, if the selected output image signal for the left eye and the selected output image signal for the right eye are not the same as the captured image signal for the left eye and the captured image signal for the right eye inputted from the imaging unit 10, it may be determined that control is performed so as to provide image display different from normal.

2. Example Operation

Figure 13:
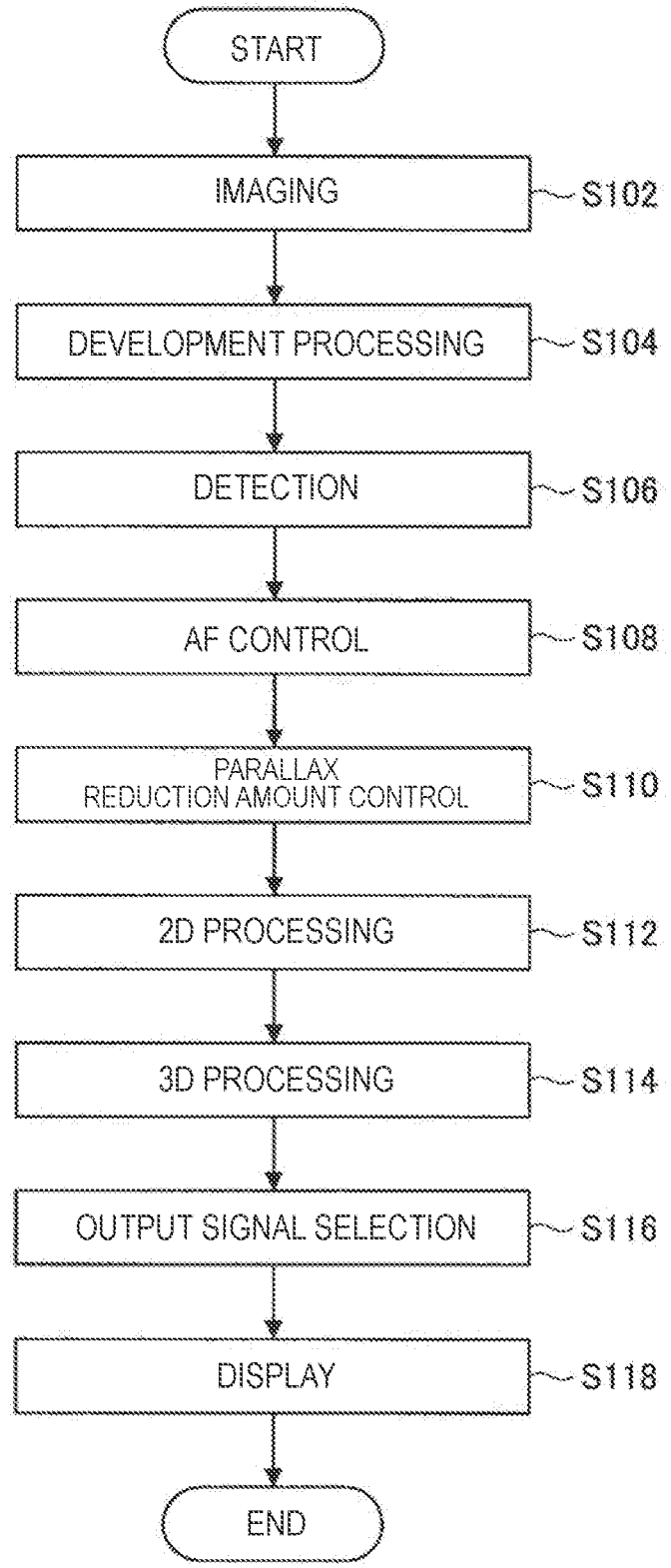
FIG. 13 is a flow chart illustrating an example operation of the information processing apparatus 1 according to the embodiment.

Example configurations of the present embodiment are described above. Next, an example operation of the present embodiment will be described with reference to FIG. 13. FIG. 13 is a flow chart illustrating an example operation of the information processing apparatus 1 according to the present embodiment.

As illustrated in FIG. 13, the imaging unit 10 first performs imaging (S102) and development processing (S104), and the captured image signal is sent from the imaging unit 10 to the display control unit 30 in the control unit 15. Moreover, the imaging unit 10 performs detection (S106) to acquire the detection value and performs AF control (S108) on the basis of the detection value.

Next, the parallax reduction amount control unit 20 in the control unit 15 controls the amount of parallax reduction on the basis of the detection value or the information associated with AF control (S110).

Next, an output image signal is outputted by processing performed by the 2D processing unit 32 in the display control unit 30 (S112), and an output image signal is further outputted by processing performed by the 3D processing unit 34 in the display control unit 30 (S114). Next, the output signal selection unit 36 selects an output image signal (S116), and the display control unit 30 controls display of the display unit 40 on the basis of the selected output image signal (S118).

Note that the processing from steps S102 to S118 described above is an example, and the present embodiment is not limited to this example. For example, the processing steps described above may be performed in an order different from the foregoing order or may be performed concurrently. Moreover, steps S102 to S118 described above may be repeated. Furthermore, in the case where the amount of parallax reduction is set and stored in advance, the stored amount of parallax reduction may be used in processing after step S110 without performing processing in step S110. Moreover, one of the processing steps in step S112 and step S114 may only be performed.

3. Modifications

An embodiment of the present disclosure is described above. Some modifications of the embodiment of the present disclosure will be described below. Note that the modifications described below may be individually applied to the embodiment of the present disclosure, or may be applied to the embodiment of the present disclosure in combination. Moreover, each modification may be applied so as to replace the configuration described in the embodiment of the present disclosure, or may be additionally applied to the configuration described in the embodiment of the present disclosure.

<3-1. Modification 1>

The above-described embodiment describes an example in which the display control unit 30 includes the 2D processing unit 32, the 3D processing unit 34, and the output signal selection unit 36, and the output signal selection unit 36 selects an output image signal from either the 2D processing unit 32 or the 3D processing unit 34. However, the present technique is not limited to this example. For example, the display control unit 30 may have only one of the function of the 2D processing unit 32 and the function of the 3D processing unit 34 described above. Moreover, the display control unit 30 may simultaneously have multiple functions selected from the foregoing example configurations of the 2D processing unit 32 or may simultaneously have multiple functions selected from the foregoing example configurations of the 3D processing unit 34 at the same time.

<3-2. Modification 2>

The above-described embodiment describes an example in which the parallax adjustment units 345L and 345R horizontally shift each pixel position in the first example configuration of the 3D processing unit 34 described with reference to FIGS. 8 and 9. In this example, there is a case where the erroneous detection of parallax in block matching by the parallax image generation unit 341 or the overlap of pixels at a position to which a pixel is shifted by the parallax adjustment units 345L and 345R may cause defective pixels. In the following description, an example in which, in case of defective pixels, the 3D processing unit 34 interpolates defective pixels (missing pixels) from surrounding pixels will be described.

Figure 14:
FIG. 14 is an explanatory diagram for describing interpolation processing on missing pixels according to Modification.

FIG. 14 is an explanatory diagram for describing interpolation processing on missing pixels. In FIG. 14, a pixel P1 of interest is a missing pixel. As illustrated in FIG. 14, non-missing pixels adjoining the pixel P1 are present adjacent to the pixel P1. Here, the 3D processing unit 34 may, for example, perform interpolation processing such that the average pixel level of non-missing pixels among pixels present adjacent to the pixel P1 becomes equal to the pixel level of the pixel P1. In the example illustrated in FIG. 14, the pixel level, p, of the pixel P1 obtained by interpolation processing is represented by the following formula (3).

$$p=(a+b+c+d+e+f)/6 \qquad (3)$$

Figure 15:
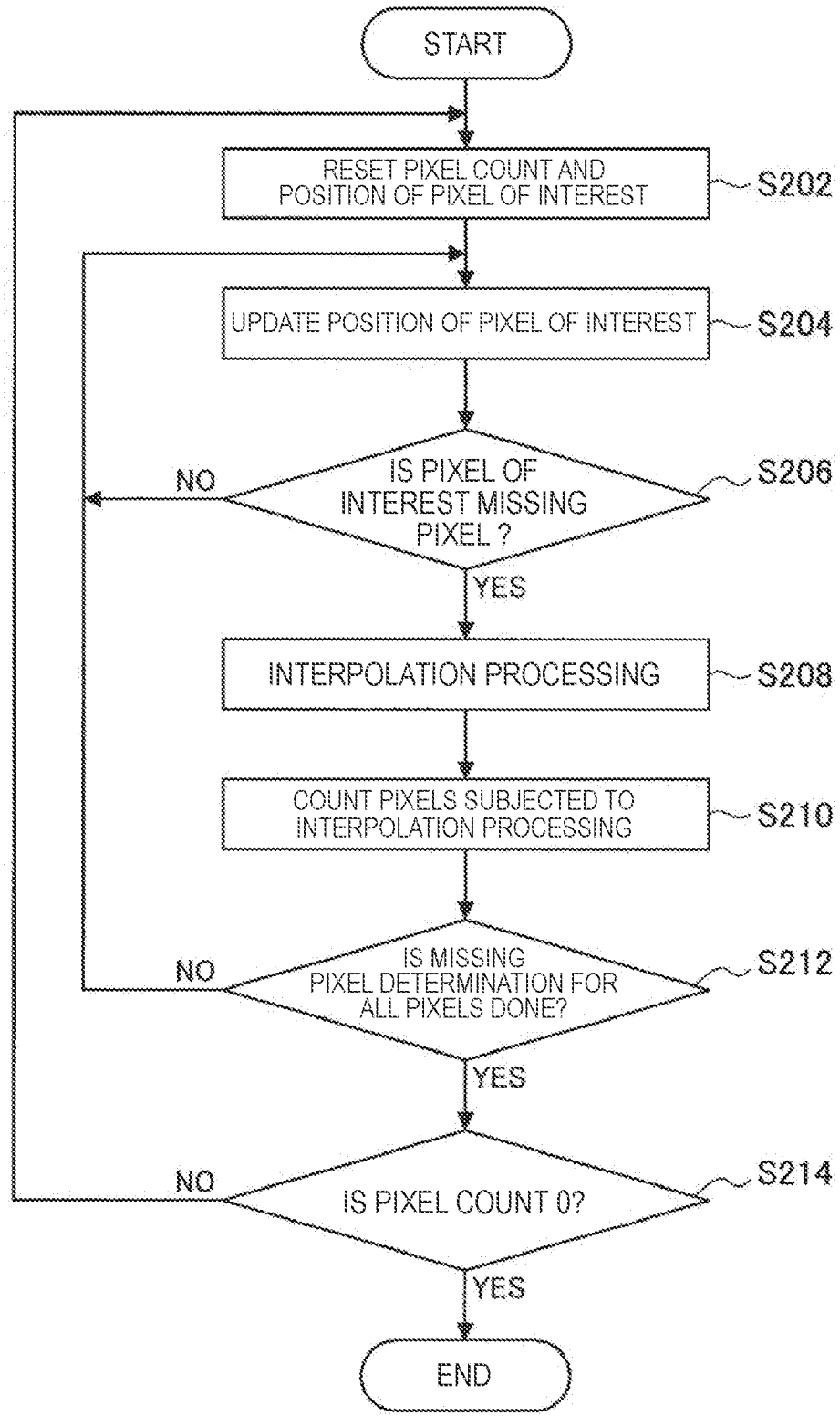
FIG. 15 is a flow chart illustrating interpolation processing on missing pixels by the 3D processing unit 34 according to the embodiment.

FIG. 15 is a flow chart illustrating interpolation processing on missing pixels by the 3D processing unit 34. First, the pixel count described below and the position of the pixel (target pixel) of interest are reset (initialized) (S202). Next, the position of the target pixel is updated (S204).

If the target pixel after update is not a missing pixel (NO in S206), processing returns to step S204. In contrast, if the target pixel after update is a missing pixel (YES in S206), the interpolation processing on the missing pixel described with reference to FIG. 14 is performed (S208).

Next, the pixels subjected to the interpolation processing are counted (S210). Furthermore, it is determined whether or not missing pixel determination for all pixels is done (S212). The processing from steps S204 to S212 is repeated until missing pixel determination for all pixels is done.

If missing pixel determination for all pixels is done (YES in S212), it is determined whether or not the pixel count is 0 with reference to the pixel count (S214). If the pixel count is not 0 (NO in S214), that is, if interpolation processing is performed at least one time in the processing from steps S204 to S212 described above, missing pixels may remain, and thus processing returns to step S202.

In contrast, if the pixel count is 0 (YES in S214), that is, if interpolation processing is performed one time in the processing from steps S204 to S212 described above, there is no missing pixel, and thus processing ends.

As described above, it is possible to interpolate missing pixels according to this modification.

<3-3. Modification 3>

The above-described embodiment describes an example in which the imaging unit 10 has the lens and the image sensors for the right eye and the left eye, but the present technique is not limited to this example.

For example, the stereoscopic imaging unit may have one image sensor. In this case, for example, the one image sensor in the imaging unit has a left pixel group and a right pixel group and outputs two image signals based on the left pixel group and the right pixel group. This configuration enables stereoscopic imaging.

Alternatively, the imaging unit 10 may have one objective lens and one relay optical system. Stereoscopic imaging may be performed as follows: a light beam transmitted by the relay optical system is divided into two beams through a diaphragm; and the beams enter the image sensor. Alternatively, the imaging unit 10 may have two objective lenses and one relay optical system. Stereoscopic imaging may be performed as follows: two optical images having parallax are transmitted by the relay optical system; and the optical images enter the image sensor.

<3-4. Modification 4>

The above-described embodiment describes an example in which the AF method associated with the imaging unit 10 is a contrast AF method, but the present technique is not limited to this example. For example, the AF method associated with the imaging unit 10 may be a phase difference AF method involving dividing light incoming from the lens into two, evaluating the degree of out-of-focus on the basis of the disparity of the images, and performing focus adjustment on the basis of the evaluation. The image sensors 102L and 102R in the imaging unit 10 in this case may each be, for example, an image plane phase difference image sensor that has phase difference pixels and performs detection by dividing light incoming from the lens into two. Moreover, the detection unit 103 may acquire a detection value on the basis of the distance between two divided images.

4. Hardware Configuration Example

Figure 16:
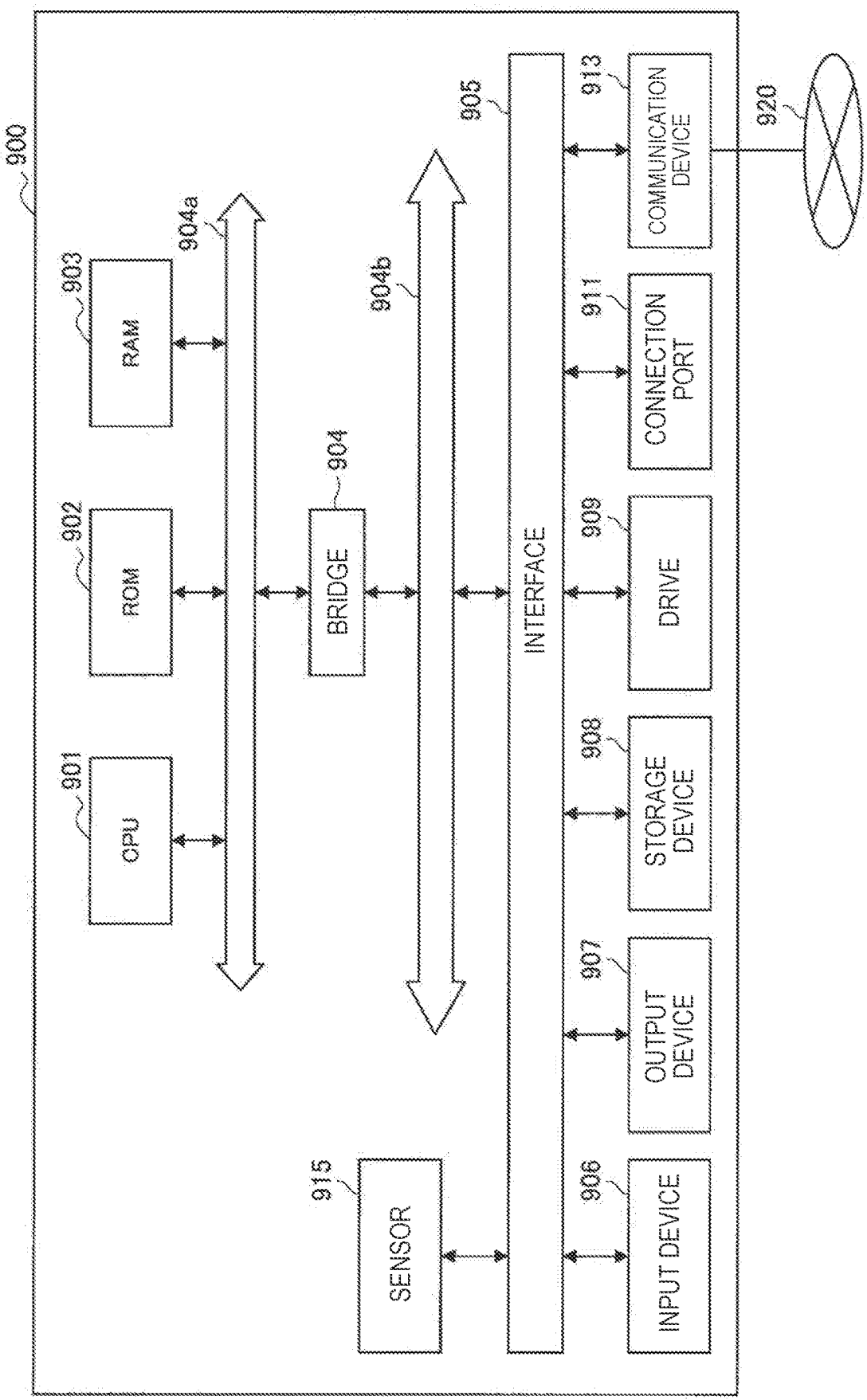
FIG. 16 is an explanatory diagram illustrating a hardware configuration example.

The embodiment of the present disclosure has been described hitherto. Finally, a hardware configuration of an information processing apparatus according to the present embodiment of the present disclosure will be described with reference to FIG. 16. FIG. 16 is a block diagram illustrating an example of the hardware configuration of the information processing apparatus according to the present embodiment of the present disclosure. Note that the information processing apparatus 1, for example, can be realized by the information processing apparatus 900 illustrated in FIG. 16. Information processing by the information processing apparatus 1 according to the present embodiment is realized according to cooperation between software and hardware described below.

As illustrated in FIG. 16, the information processing apparatus 900 includes a central processing unit (CPU) 901, a read only memory (ROM) 902, a random access memory (RAM) 903, and a host bus 904a. In addition, the information processing apparatus 900 includes a bridge 904, an external bus 904b, an interface 905, an input device 906, an output device 907, a storage device 908, a drive 909, a connection port 911, a communication device 913, and a sensor 915. The information processing apparatus 900 may include a processing circuit such as a DSP or an ASIC instead of the CPU 901 or along therewith.

The CPU 901 functions as an arithmetic processing device and a control device and controls the overall operation in the information processing apparatus 900 according to various programs. Further, the CPU 901 may be a microprocessor. The ROM 902 stores programs, operation parameters, and the like used by the CPU 901. The RAM 903 temporarily stores programs used in execution of the CPU 901, parameters appropriately changed in the execution, and the like. The CPU 901 may form the control unit 15 illustrated in FIG. 11, for example.

The CPU 901, the ROM 902, and the RAM 903 are mutually connected by the host bus 904a including a CPU bus and the like. The host bus 904a is connected with the external bus 904b such as a peripheral component interconnect/interface (PCI) bus via the bridge 904. Further, the host bus 904a, the bridge 904, and the external bus 904b are not necessarily separately configured and such functions may be mounted in a single bus.

The input device 906 is realized by a device through which a user inputs information, such as a mouse, a keyboard, a touch panel, a button, a microphone, a switch, and a lever, for example. In addition, the input device 906 may be a remote control device using infrared ray or other electric waves, or external connection equipment such as a cellular phone or a PDA corresponding to an operation of the information processing apparatus 900, for example. Furthermore, the input device 906 may include an input control circuit or the like which generates an input signal on the basis of information input by the user using the aforementioned input means and outputs the input signal to the CPU 901, for example. The user of the information processing apparatus 900 may input various types of data or order a processing operation for the information processing apparatus 900 by operating the input device 906.

The output device 907 is formed by a device that may visually or aurally notify the user of acquired information.

As such devices, there are a display device such as a CRT display device, a liquid crystal display device, a plasma display device, an EL display device, or a lamp, a sound output device such as a speaker and a headphone, a printer device, and the like. The output device 907 outputs results acquired through various processes performed by the information processing apparatus 900, for example. Specifically, the display device visually displays results acquired through various processes performed by the information processing apparatus 900 in various forms such as text, images, tables, and graphs. On the other hand, the sound output device converts audio signals including reproduced sound data, audio data, and the like into analog signals and aurally outputs the analog signals. The aforementioned display device may form the display unit 40 illustrated in FIG. 1, for example.

The storage device 908 is a device for data storage, formed as an example of a storage unit of the information processing apparatus 900. For example, the storage device 908 is realized by a magnetic storage device such as an HDD, a semiconductor storage device, an optical storage device, a magneto-optical storage device, or the like. The storage device 908 may include a storage medium, a recording device for recording data on the storage medium, a reading device for reading data from the storage medium, a deletion device for deleting data recorded on the storage medium, and the like. The storage device 908 stores programs and various types of data executed by the CPU 901, various types of data acquired from the outside, and the like.

The drive 909 is a reader/writer for storage media and is included in or externally attached to the information processing apparatus 900. The drive 909 reads information recorded on a removable storage medium such as a magnetic disc, an optical disc, a magneto-optical disc, or a semiconductor memory mounted thereon, and outputs the information to the RAM 903. In addition, the drive 909 may write information on the removable storage medium.

The connection port 911 is an interface connected with external equipment and is a connector to the external equipment through which data may be transmitted through a universal serial bus (USB) and the like, for example.

The communication device 913 is a communication interface formed by a communication device for connection to a network 920 or the like, for example. The communication device 913 is a communication card or the like for a wired or wireless local area network (LAN), long term evolution (LTE), Bluetooth (registered trademark), or wireless USB (WUSB), for example. In addition, the communication device 913 may be a router for optical communication, a router for asymmetric digital subscriber line (ADSL), various communication modems, or the like. For example, the communication device 913 may transmit/receive signals and the like to/from the Internet and other communication apparatuses according to a predetermined protocol such as, for example, TCP/IP.

Further, the network 920 is a wired or wireless transmission path of information transmitted from devices connected to the network 920. For example, the network 920 may include a public circuit network such as the Internet, a telephone circuit network, or a satellite communication network, various local area networks (LANs) including Ethernet (registered trademark), a wide area network (WAN), and the like. In addition, the network 920 may include a dedicated circuit network such as an internet protocol-virtual private network (IP-VPN).

The sensor 915 corresponds to various types of sensors such as an acceleration sensor, a gyro sensor, a geomagnetic sensor, a light sensor, a sound sensor, a distance measuring sensor, and a force sensor, for example. The sensor 915 acquires information regarding a state of the information processing apparatus 900 itself, such as an attitude and a movement speed of the information processing apparatus 900, and information regarding a surrounding environment of the information processing apparatus 900, such as brightness and noise of the periphery of the information processing apparatus 900. In addition, the sensor 915 may include a GPS sensor that receives a GPS signal, and measures latitude, longitude, and altitude of the device.

Hereinbefore, an example of a hardware configuration capable of realizing the functions of the information processing apparatus 900 according to this embodiment is shown. The respective components may be implemented using universal members, or may be implemented by hardware specific to the functions of the respective components. Accordingly, according to a technical level at the time when the embodiments are executed, it is possible to appropriately change hardware configurations to be used.

In addition, a computer program for realizing each of the functions of the information processing apparatus 900 according to the present embodiment as described above may be created, and may be mounted in a PC or the like. Furthermore, a computer-readable recording medium on which such a computer program is stored may be provided. The recording medium is a magnetic disc, an optical disc, a magneto-optical disc, a flash memory, or the like, for example. Further, the computer program may be delivered through a network, for example, without using the recording medium. Moreover, the number of computers that execute the computer program is not limited. For example, the computer program may be executed by a plurality of computers (e.g., a plurality of servers) in cooperation with each other.

5. Conclusion

According to the embodiment of the present disclosure as described above, it is possible to alleviate discomfort that the user experiences during operation of autofocus.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the above-described embodiment describes an example in which the information processing apparatus 1 includes the imaging unit 10, the control unit 15, and the display unit 40, but the present technique is not limited to this example. For example, different devices may respectively have the functions of the imaging unit 10, the control unit 15, and the display unit 40. For example, an information processing system in which an imaging device having the function of the imaging unit 10, an information processing device having the function of the control unit 15, and a display device having the function of the display unit 40 are connected to each other via a network or the like may also be included in the technical scope of the present disclosure.

In addition, the present technique may be applied to, for example, 3D endoscopes and 3D microscopes for medical use. In the field in which a 3D endoscope or a 3D microscope for medical use is used, the user often observes the captured image while capturing the image, and the distance between an object of observation (subject) and the 3D endoscope or the 3D microscope tends to change, and thus AF often works. For this, the present technique may be very effective. Of course, the present technique is not necessarily applied to the foregoing devices, and the present technique may be applied to various devices associated with stereoscopic imaging.

In addition, steps in the above-described embodiment need not be always processed in chronological order in accordance with the order described as a flow chart. For example, steps in the processes in the above-described embodiment may be processed in an order different from the order described as a flow chart, or may be concurrently processed.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:

a control unit configured to control display on the basis of a detection value indicating a focus state of a lens acquired from a stereoscopic imaging unit, and a captured image signal for a left eye and a captured image signal for a right eye acquired from the imaging unit.

(2)

The information processing apparatus according to (1), in which the control unit controls the display on the basis of an amount of parallax reduction, which indicates a degree at which parallax associated with the display is to be reduced.

(3)

The information processing apparatus according to (2), in which the control unit controls the amount of parallax reduction on the basis of the detection value.

(4)

The information processing apparatus according to (3), in which the detection value increases as a degree of focus of the lens increases, and the control unit performs control such that the amount of parallax reduction decreases as the detection value increases.

(5)

The information processing apparatus according to (3), in which the control unit controls the amount of parallax reduction on the basis of a movement start time of the lens in autofocus control performed on the basis of the detection value.

(6)

The information processing apparatus according to any one of (3) to (5), in which the control unit controls the amount of parallax reduction on the basis of a movement speed of the lens in autofocus control performed on the basis of the detection value.

(7)

The information processing apparatus according to any one of (3) to (6), in which the control unit controls the display by performing parallax adjustment processing on a captured image for the left eye and a captured image for the right eye so as to reduce parallax associated with the display on the basis of matching between the captured image for the left eye obtained from the captured image signal for the left eye and the captured image for the right eye obtained from the captured image signal for the right eye.

(8)

The information processing apparatus according to (7), in which the control unit generates a parallax image signal indicating parallax at each position in the captured image for the left eye and the captured image for the right eye by means of the matching, generates a parallax adjustment image signal for reducing parallax at each position on the basis of the parallax image signal and the amount of parallax reduction, and performs the parallax adjustment processing on the basis of the parallax adjustment image signal.

(9)

The information processing apparatus according to (8), in which the control unit specifies an amount of shift in entire image between the captured image for the left eye and the captured image for the right eye by means of the matching, specifies an amount of parallax adjustment on the basis of the amount of shift and the amount of parallax reduction, and performs the parallax adjustment processing on the basis of the amount of parallax adjustment.

(10)

The information processing apparatus according to any one of (7) to (9), in which the control unit selects which one of display control based on the parallax adjustment processing and other display control is performed in accordance with parallax detection information obtained from a sum of absolute differences in the matching.

(11)

The information processing apparatus according to any one of (3) to (10), in which the control unit controls the display such that a display image for the left eye and a display image for the right eye in the display are same images in a case where the amount of parallax reduction is larger than a predetermined threshold.

(12)

The information processing apparatus according to any one of (3) to (10), in which the control unit causes display of an image formed by combining a captured image for the left eye obtained from the captured image signal for the left eye and a captured image for the right eye obtained from the captured image signal for the right eye, in accordance with the amount of parallax reduction.

(13)

The information processing apparatus according to any one of (3) to (10), in which the control unit causes display of an image formed by reducing a pixel level of any one of a captured image for the left eye obtained from the captured image signal for the left eye and a captured image for the right eye obtained from the captured image signal for the right eye, in accordance with the amount of parallax reduction.

(14)

The information processing apparatus according to (3), in which the control unit performs blur processing in accordance with the amount of parallax reduction.

(15)

The information processing apparatus according to (3), further including storage units configured to store the captured image signal for the left eye and the captured image signal for the right eye, in which the control unit causes display of an image obtained from the captured image signal for the left eye and the captured image signal for the right eye that are stored in the storage units, on the basis of the amount of parallax reduction.

(16)
The information processing apparatus according to (15), in which the control unit causes display of an image obtained from the captured image signal for the left eye and the captured image signal for the right eye based on imaging just before start of movement of the lens in autofocus control performed on the basis of the detection value, the captured image signal for the left eye and the captured image signal for the right eye being stored in the storage units.

(17)
The information processing apparatus according to (1), in which the control unit controls the display in accordance with a user's input.

(18)
An information processing method including:
controlling display on the basis of a detection value indicating a focus state of a lens acquired from a stereoscopic imaging unit, and a captured image signal for a left eye and a captured image signal for a right eye acquired from the imaging unit.

(19)
A program for causing a computer to realize:
a function of controlling display on the basis of a detection value indicating a focus state of a lens acquired from a stereoscopic imaging unit, and a captured image signal for a left eye and a captured image signal for a right eye acquired from the imaging unit.

(20)
An information processing system including:
a stereoscopic imaging device;
a stereoscopic display device; and
a control unit configured to control display of the display device on the basis of a detection value indicating a focus state of a lens acquired from the imaging device, and a captured image signal for a left eye and a captured image signal for a right eye acquired from the imaging device.

REFERENCE SIGNS LIST 1 information processing apparatus
10 imaging unit
15 control unit
20 parallax reduction amount control unit
30 display control unit
32 2D processing unit
34 3D processing unit
36 output signal selection unit
40 display unit
101L, 101R lens
102L, 102R image sensor
103 detection unit
104 AF control unit
105 lens drive unit
106 development processing unit
322 selection unit
324L, 324R gain adjustment unit
326 adder unit
328 gain adjustment unit
341 parallax image generation unit
343 parallax adjustment image generation unit
345L, 345R parallax adjustment unit
347 matching unit
349L, 349R image shift adjustment unit
351L, 351R blurring unit
353L, 353R storage unit
355L, 355R output selection unit

The invention claimed is:

1. An information processing apparatus, comprising:
a control unit configured to:
acquire, from an imaging unit, a captured image signal for a left eye and a captured image signal for a right eye;
acquire a detection value based on the captured image signal for the left eye and the captured image signal for the right eye acquired from the imaging unit, wherein the detection value indicates a focus state of a lens of the imaging unit;
control an amount of parallax reduction that indicates a degree at which parallax associated with a display is to be reduced, wherein the control of the amount of parallax reduction includes:
increase in the amount of parallax reduction for a specific time from a movement start time of the lens in an autofocus control, wherein the autofocus control is based on the detection value; and
decrease in the amount of parallax reduction after the specific time from the movement start time of the lens;
output a signal for the left eye based on multiplication of the captured image signal for the left eye by a first gain;
output a signal for the right eye based on multiplication of the captured image signal for the right eye by a second gain, wherein the first gain and the second gain are variable based on the amount of parallax reduction;
output a combination of the signal for the left eye and the signal for the right eye as an output image signal for the right eye;
output the captured image signal for the left eye as an output image signal for the left eye; and
control the display on a display screen based on the output image signal for the left eye and the output image signal for the right eye.

2. The information processing apparatus according to claim 1, wherein
the control unit is further configured to decrease the amount of parallax reduction based on an increase in the detection value, and
the increase in the detection value is based on an increase in a degree of focus of the lens.

3. The information processing apparatus according to claim 1, wherein the control unit is further configured to:
increase the amount of parallax reduction based on an increase in a movement speed of the lens in the autofocus control.

4. The information processing apparatus according to claim 1, wherein the control unit is further configured to:
perform a matching process between a captured image for the left eye and a captured image for the right eye;
perform a parallax adjustment process on the captured image for the left eye and the captured image for the right eye based on the matching process;
reduce the parallax associated with the display based on the parallax adjustment process, wherein
the captured image for the left eye corresponds to the captured image signal for the left eye, and
the captured image for the right eye corresponds to the captured image signal for the right eye; and
control the display on the display screen based on the parallax adjustment process.

5. The information processing apparatus according to claim 4, wherein the control unit is further configured to:

generate a parallax image signal indicating the parallax at each position in each of the captured image for the left eye and the captured image for the right eye based on the matching process;

generate a parallax adjustment image signal based on the parallax image signal and the amount of parallax reduction; and reduce the parallax based on the parallax adjustment image signal.

6. The information processing apparatus according to claim 5, wherein the control unit is further configured to:

specify an amount of shift in each pixel position of the captured image for the left eye and the captured image for the right eye based on the matching process;

specify an amount of parallax adjustment based on the amount of shift and the amount of parallax reduction; and perform the parallax adjustment process based on the amount of parallax adjustment.

7. The information processing apparatus according to claim 4, wherein the control unit is further configured to:

obtain parallax detection information based on a sum of absolute differences in the matching process; and control the display on the display screen based on the parallax detection information.

8. The information processing apparatus according to claim 1, wherein the control unit is further configured to:

determine the amount of parallax reduction is larger than a specific threshold; and control, based on the determination, the display on the display screen such that a display image for the left eye and a display image for the right eye in the display are same.

9. The information processing apparatus according to claim 1, wherein the control unit is further configured to:

reduce a pixel level of one of a captured image for the left eye or a captured image for the right eye based on the amount of parallax reduction; and control display of a specific image on the display screen based on the reduction of the pixel level, wherein the captured image for the left eye corresponds to the captured image signal for the left eye, and the captured image for the right eye corresponds to the captured image signal for the right eye.

10. The information processing apparatus according to claim 1, wherein the control unit is further configured to perform a blur process based on the amount of parallax reduction.

11. The information processing apparatus according to claim 1, further comprising a storage unit configured to store the captured image signal for the left eye and the captured image signal for the right eye, wherein the control unit is further configured to:

obtain an image from one of the stored captured image signal for the left eye or the stored captured image signal for the right eye based on the amount of parallax reduction; and control display of the obtained image on the display screen.

12. The information processing apparatus according to claim 11, wherein the control unit is further configured to acquire the captured image signal for the left eye and the captured image signal for the right eye before a start of movement of the lens in the autofocus control.

13. The information processing apparatus according to claim 1, wherein the control unit is further configured to control the display on the display screen based on a user input.

14. An information processing method, comprising:

acquiring, from an imaging unit, a captured image signal for a left eye and a captured image signal for a right eye;

acquiring a detection value based on the captured image signal for the left eye and the captured image signal for the right eye acquired from the imaging unit, wherein the detection value indicates a focus state of a lens of the imaging unit;

controlling an amount of parallax reduction that indicates a degree at which parallax associated with a display is to be reduced, wherein the control of the amount of parallax reduction includes:

increasing the amount of parallax reduction for a specific time from a movement start time of the lens in an autofocus control, wherein the autofocus control is based on the detection value; and decreasing the amount of parallax reduction after the specific time from the movement start time of the lens;

outputting a signal for the left eye based on multiplication of the captured image signal for the left eye by a first gain;

outputting a signal for the right eye based on multiplication of the captured image signal for the right eye by a second gain, wherein the first gain and the second gain are variable based on the amount of parallax reduction;

outputting a combination of the signal for the left eye and the signal for the right eye as an output image signal for the right eye;

outputting the captured image signal for the left eye as an output image signal for the left eye; and controlling the display on a display screen based on the output image signal for the left eye and the output image signal for the right eye.

15. A non-transitory computer-readable medium having stored thereon, computer-executable instructions, which when executed by a processor of a control device, cause the processor to execute operations, the operations comprising:

acquiring, from an imaging unit, a captured image signal for a left eye and a captured image signal for a right eye;

acquiring a detection value based on the captured image signal for the left eye and the captured image signal for the right eye acquired from the imaging unit, wherein the detection value indicates a focus state of a lens of the imaging unit;

controlling an amount of parallax reduction that indicates a degree at which parallax associated with a display is to be reduced, wherein the control of the amount of parallax reduction includes:

increasing the amount of parallax reduction for a specific time from a movement start time of the lens in an autofocus control, wherein the autofocus control is based on the detection value; and decreasing the amount of parallax reduction after the specific time from the movement start time of the lens;

outputting a signal for the left eye based on multiplication of the captured image signal for the left eye by a first gain;

outputting a signal for the right eye based on multiplication of the captured image signal for the right eye by a second gain, wherein the first gain and the second gain are variable based on the amount of parallax reduction;

outputting a combination of the signal for the left eye and the signal for the right eye as an output image signal for the right eye;

outputting the captured image signal for the left eye as an output image signal for the left eye; and controlling the display on a display screen based on the output image signal for the left eye and the output image signal for the right eye.

16. An information processing system, comprising:

a stereoscopic imaging device;

a stereoscopic display device; and a control unit configured to:

acquire, from the stereoscopic imaging device, a captured image signal for a left eye and a captured image signal for a right eye;

acquire a detection value based on the captured image signal for the left eye and the captured image signal for the right eye acquired from the stereoscopic imaging device, wherein the detection value indicates a focus state of a lens of the stereoscopic imaging device;

control an amount of parallax reduction that indicates a degree at which parallax associated with a display is to be reduced, wherein the control of the amount of parallax reduction includes:

increase in the amount of parallax reduction for a specific time from a movement start time of the lens in an autofocus control, wherein the autofocus control is based on the detection value; and decrease in the amount of parallax reduction after the specific time from the movement start time of the lens;

output a signal for the left eye based on multiplication of the captured image signal for the left eye by a first gain;

output a signal for the right eye based on multiplication of the captured image signal for the right eye by a second gain, wherein the first gain and the second gain are variable based on the amount of parallax reduction;

output a combination of the signal for the left eye and the signal for the right eye as an output image signal for the right eye;

output the captured image signal for the left eye as an output image signal for the left eye; and control the display on the stereoscopic display device based on the output image signal for the left eye and the output image signal for the right eye.

* * * * *